(12) United States Patent
Vito et al.

(10) Patent No.: US 7,300,455 B2
(45) Date of Patent: *Nov. 27, 2007

(54) INTRAVASCULAR DEVICE FOR AXIALLY STRETCHING BLOOD VESSELS

(75) Inventors: Raymond P. Vito, Atlanta, GA (US); Jack C. Griffis, III, Decatur, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/371,663

(22) Filed: Mar. 9, 2006

(65) Prior Publication Data

US 2006/0271162 A1 Nov. 30, 2006

Related U.S. Application Data

(63) Continuation of application No. 10/093,715, filed on Mar. 7, 2002, now Pat. No. 7,018,402.

(60) Provisional application No. 60/274,703, filed on Mar. 9, 2001.

(51) Int. Cl.
*A61F 2/06* (2006.01)
(52) U.S. Cl. ............... 623/1.11; 604/102.02; 604/102.03; 604/102.04; 604/102.05
(58) Field of Classification Search ...... 623/1.11–1.22; 604/101.01–5
See application file for complete search history.

(56) References Cited

U.S. PATENT DOCUMENTS 4,911,163 A * 3/1990 Fina ............... 606/127
4,978,348 A 12/1990 Ilizarov
5,078,726 A 1/1992 Kreamer
5,162,529 A * 11/1992 Lantzsch et al. ............ 544/298
5,344,425 A 9/1994 Sawyer
5,549,664 A 8/1996 Hirata et al.

(Continued)

FOREIGN PATENT DOCUMENTS

WO  WO 99/42528  8/1999

OTHER PUBLICATIONS

Bergsma, et al., "Low Recurrence of Angina Pectoris After Coronary Artery Bypass Graft Surgery With Bilateral internal Thoracic and Right Gastroepiptoic Arteries," *Circulation* 97(24):2402-05 (1998).

(Continued)

*Primary Examiner*—Vy Q. Bui
(74) *Attorney, Agent, or Firm*—Sutherland Asbill & Brennan LLP (57) ABSTRACT

Intravascular devices are provided for forming a vascular graft by axially distending a blood vessel to induce growth. These devices advantageously can be implanted via a catheter, thereby eliminating the need for a more invasive implantation procedure when the stretching is to be done in vivo. The implantable medical device for distending a blood vessel to induce axial growth of the blood vessel includes an intravascular stretching mechanism securable to an interior luminal surface of a blood vessel in vivo, and a means for operating the intravascular stretching mechanism in vivo to cause the vessel to stretch and grow axially. The stretching mechanism can include a pair of wires or stents that engage the blood vessel wall, and components of the stretching mechanism may include a shape memory material.

19 Claims, 7 Drawing Sheets

U.S. PATENT DOCUMENTS

| | | | |
|---|---|---|---|
| 5,702,419 | A | 12/1997 | Berry et al. |
| 5,713,917 | A | 2/1998 | Leonhardt et al. |
| 5,769,893 | A | 6/1998 | Shah |
| 5,879,713 | A | 3/1999 | Roth et al. |
| 5,879,875 | A | 3/1999 | Wiggins et al. |
| 5,888,720 | A | 3/1999 | Mitrani |
| 5,899,936 | A | 5/1999 | Goldstein |
| 5,902,228 | A | 5/1999 | Schulsinger et al. |
| 6,033,436 | A | 3/2000 | Steinke et al. |
| 6,160,084 | A | 12/2000 | Langer et al. |
| 6,193,744 | B1 | 2/2001 | Ehr et al. |
| 6,322,553 | B1 | 11/2001 | Vito et al. |
| 6,641,576 | B1 | 11/2003 | Vito et al. |
| 6,663,617 | B1 | 12/2003 | Vito et al. |
| 6,899,669 | B2 | 5/2005 | Vito et al. |
| 6,991,628 | B2 | 1/2006 | Vito et al. |

OTHER PUBLICATIONS

Birukov, et al., "Stretch Affects Phenotype and Proliferation of Vascular Smooth Muscle Cells," *Mol Cell Biochem.* 144(2):131-39(1995).

Cooley, "Coronary Bypass Grafting With Bilateral Internal Thoracic Arteries and the Right Gastropiploic Artery," *Circulation* 97(24):2384-85 (1998).

Cohen, et al., "Acute Intraoperative Arterial Lengthening for Closure of Large Vascular Gaps," *Plastic and Reconstructive Surgery*, pp. 463-468 (1992).

Conklin, B., "Viability of Porcine Common Carotid Arteries in a Novel Organ Culture System", *MS Thesis*, Georgia Institute of Technology, 1997.

Costa, et al., "Increased Elastin Synthesis by Cultured Bovine Aortic Smooth Muscle Cells Subjected to Repetitive Mechanical Stretching," *Faseb J.*, 5: A 1609, 7191 (1991).

Fu, et al., "Biorheological Features of Some Soft Tissues Under a Surgical Tissue Expansion Procedure," Biortheological Study on Tissue Expansion, 34:281-93 (1997).

Han, et al., "Axial Stretch Increases Cell Proliferation in Arteries in Organ Culture", *Advances in Bioengineering, ASME, BED*48:63-64 (2000).

Ippolito, et al., "Histology and Ultrasound of Arteries, Veins, and Peripheral Nerves During Limb Lengthening," *Clinical Orthopaedics and Related Research*, 308:54-63 (1994).

Kanda, et al., "Phenotypic Reversion of Smooth Muscle Cells in Hybrid Vascular Prostheses," *Cell Transplantation* 4(6):587-95 (1995).

Kolpakov, et al, "Effect of Mechanical Forces on Growth and Matrix Protein Synthesis in the In Vitro Pulmonary Artery," *Circulation Research*, 77:823-31 (1995).

Leung, et al., "Cyclic Stretching Stimulates Synthesis of Matrix Components by Arterial Smooth Muscle Cells in Vitro," *Science* 191:475-77 (1976).

Moore, et al., "A Device of Subjecting Vascular Endotheilal Cells to Both Fluid Shear Stress and Circumferential Cyclic Stretch," *Annals of Biomedical Engineering*, 22:416-22 (1994).

Ruiz-Razura, et al., "Clinical Applications of Acute Intraoperative Arterial Elongation," *J. Reconstructive Microsurgery*, 9:335-40 (1993).

Ruiz-Razura, et al., "Acute Intraoperative Arterial Elongation: Histologic, Morphologic, and Vascular Reactivity Studies," *J. Reconstructive Microsurgery*, 10(6):367-73 (1994).

Ruiz-Razura, et al., "Tissue Expanders in Microvascular Surgery Acute Intraoperative Arterial Elongation," *Surgical Forum*, pp. 610-614 (1989).

Stark, et al., "Rapid Elongation of Arteries and Veins in Rats with a Tissue Expander," Plastic & Reconstructive Surgery, 80(4):570-78 (1987).

* cited by examiner

INTRAVASCULAR DEVICE FOR AXIALLY STRETCHING BLOOD VESSELS

CROSS-REFERENCE TO RELATED APPLICATIONS

This is a continuation of U.S. patent application No. 10/093,715, filed Mar. 7, 2002, now U.S. Pat. No. 7,018,402 which claims benefit under 35 U.S.C. § 119 of U.S. Provisional Application No. 60/274,703, filed Mar. 9, 2001. These applications are incorporated herein by reference

BACKGROUND OF THE INVENTION

The present invention is generally in the area of methods and devices for producing vascular tissue grafts from living vascular tissue, and particularly for making autologous grafts.

Vascular grafts are commonly used by surgeons to bypass obstructions to blood flow caused by the presence of atherosclerotic plaques. Vascular grafts also are used in other applications such as providing arterial-venous shunts in dialysis patients, vascular repair or replacement and treating aneurysms. Grafts for bypass are often, but not exclusively, used in the coronary arteries, the arteries that supply blood to the heart.

The materials used to construct a vascular graft usually are either synthetic or of biological origin, but combinations of synthetic and biological materials are under development. The most widely used biological vascular grafts are autologous saphenous vein or mammary artery. Some common synthetic grafts are made of polytetrafluoroethylene (PTFE) (e.g., GORTEX™) or polyester (e.g., DACRON™). Autologous grafts have generally been used more successfully than synthetic grafts. Autologous grafts remain patent (functional) much longer than synthetic grafts, and saphenous veins often fail in less than five years. The short lifetime of synthetic grafts is especially evident with small diameter (less than 7 mm diameter) grafts, as most small diameter synthetic grafts occlude within one to two years or less.

Small diameter vascular grafts are particularly used in coronary artery bypass surgery. Internal mammary artery (IMA) is the autologous graft of choice, because it typically has a longer life than venous grafts (95% patent at five years versus 85% patent at two years). Mammary arterial tissue, however, is difficult to harvest, is typically not available in lengths sufficient for multiple bypasses, and its removal can result in problems such as problematic wound healing. Moreover, obtaining sufficient venous tissue for repairing an occluded artery can be problematic in patients with venous conditions such as varicose veins and especially in second or third surgeries in the same patient. Literature also suggests that IMA used in bypass procedures either fails soon after transplantation or remains patent indefinitely. See, e.g., Bergsma, et al., *Circulation* 97(24):2402-05 (1998); Cooley, *Circulation* 97(24):2384-85 (1998).

Other arteries such as the gastroepipolic, gastric, radial, and splenic also are used in coronary bypass procedures. In some cases, autologous or homologous saphenous vein preserved by freezing or other processes is used. A recent American Heart Association/American College of Cardiology consensus document strongly recommends a move to total arterial revascularization (Eagle, et al. "ACC/AHA Guidelines for coronary artery bypass graft surgery: A report of the American College of Cardiology/American Heart Association Task Force on Practice Guidelines", Committee to Revise the 1991 Guidelines for Coronary Artery Bypass Graft Surgery, American College of Cardiology/American Heart Association, *J. Am. Coll. Cardiol.*, 34(4):1262-347 (1999)).

Development of a longer lasting small-diameter vascular graft is the subject of much academic and industrial research. One current approach is to combine cell culture and biomaterials technologies to make a living, "tissue engineered" graft. This effort, however, is hindered by the requirements of a successful graft. The graft should be self-repairing, non-immunogenic, non-toxic, and non-thrombogenic; should have a compliance comparable to the artery being repaired; should be easily sutured by a surgeon; and should not require any special techniques or handling procedures. Grafts having these characteristics are difficult to achieve. Despite the substantial effort to date and the potential for significant financial reward, academic and industrial investigators have failed to produce graft materials that have demonstrated efficacy in human testing.

Efforts to avoid or minimize the need for vascular grafts for repair of otherwise healthy vascular tissue have been described. For example, Ruiz-Razura et al., *J. Reconstructive Microsurgery*, 10(6):367-73 (1994) and Stark et al., *Plastic & Reconstructive Surgery*, 80(4):570-78 (1987) disclose the use of a round microvascular tissue expander for acute arterial elongation to examine the effects on the tissue of such acute hyperextension. The expander is a silicone balloon that is placed under the vessel to be elongated. The balloon is filled with saline over a very short period, causing acute stretching and elongation of the vessel. The method is purported to be effective for closure of arterial defects up to 30 mm without the need for a vein graft. These techniques are appropriate for trauma, but are not used for restoring blood flow in vessels that are occluded, for example by disease, which are treated by surgically bypassing the obstruction with a graft. The disclosed methods and devices fail to provide an autologous graft or versatile substitute. Moreover, the acute stretching may damage the vessel.

It has been demonstrated, however, that axial stretching can increase smooth muscle cell proliferation in an intact blood vessel, thereby substantially enhancing blood vessel growth. See Conklin, "*Viability of Porcine Common Carotid Arteries in a Novel Organ Culture System*" MS Thesis, Georgia Institute of Technology, 1997); Han, et al., "Axial Stretch Increases Cell Proliferation in Arteries in Organ Culture", *Advances in Bioengineering ASME, BED* 48:63-64 (2000).

PCT WO 99/60952 to Georgia Tech Research Corporation and U.S. Pat. No. 6,322,553 to Vito describe devices and methods for producing axial growth by mechanically stimulating a blood vessel using axial distention. These devices anchor to exterior surfaces of the blood vessels, and consequently their use in vivo is necessarily invasive, at least requiring endoscopic surgery. The size of the devices also may limit the sites that are suitable for implantation. It would be advantageous to develop devices and methods that are less invasive and more easily installed and used in vivo. It would also be tremendously beneficial to the patient to be able to eliminate the need for surgery before removal of the grown blood vessel for use as an autologous graft. It would be desirable to provide minimally- or non-invasive devices and methods for stretching and growing blood vessels in vivo. It also would be desirable to provide simple devices and methods for creating natural blood vessel suitable for grafting, and for making an autologous blood vessel graft with fewer surgeries.

SUMMARY OF THE INVENTION

Intravascular devices and methods are provided for forming a vascular graft by axially distending a blood vessel to stimulate vessel growth. These devices advantageously can be implanted via a catheter, thereby eliminating the need for a more invasive implantation procedure when the stretching is to be done in vivo. Where the vessel donor is the recipient of the graft, a totally autologous, living vascular graft is provided.

The device for axially distending a blood vessel to induce growth of the vessel includes an intravascular stretching mechanism attachable directly to an interior lumen portion of the blood vessel, and a means for operating the stretching mechanism to cause the vessel to distend axially. In a preferred embodiment, the intravascular stretching mechanism is composed of an anchoring wire and a stretching wire, wherein the distal end portions of these wires are separately anchorable to the interior lumen portion at positions axially remote from one another. The device may further include a catheter having at least two lumens that are suitable for delivering the stretching wire and the anchor wire into the interior lumen portion of the blood vessel. The catheter and wires can be provided as a kit or an assembled device.

The distal end portion of the anchoring wire, the distal end portion of the stretching wire, or both, can include or be formed of a shape memory material. Preferably, the shape memory material comprises nickel-titanium or a shape memory polymer. In operation of such an embodiment, the shape memory material changes shape in response to an effective temperature change, such as the temperature increase experienced following insertion of the material into a live mammalian body. The shape change, for example, can cause the distal end portion of the stretching wire to change from a substantially straight form into a spiral configuration which frictionally engages a first position in the interior lumen portion of the blood vessel and then can cause the distal end portion of the anchoring wire to change from a substantially straight form into a spiral configuration which engages a second position in the interior lumen portion of the blood vessel. Stretching forces can then be applied to the wire(s) to push/pull the distal portions away from each other.

In one variation, the stretching wire can further include an intermediary portion which changes shape, for example by use of a shape memory material, from a substantially straight form into a helical configuration which functions as a compression spring to impart the stretching forces.

The means for operating the stretching mechanism can include a prime mover that is mechanically, electromechanically, or hydraulically driven. This operating means can cause the axial stretching force to be applied to the vessel in a continuous, intermittent, or cyclical manner, and applied rectilinearly, curvilinearly, or in a combination thereof. The device can also include a controller for controlling the means for operating the stretching mechanism.

In another preferred embodiment, the intravascular stretching mechanism comprises a first stent, a second stent, and a compression spring operably connected to the first stent and the second stent, wherein the first and second stents are separately anchorable to the interior lumen portion at positions axially remote from one another. In this embodiment, the first stent, the second stent, the compression spring, or a combination thereof, can include a shape memory material, such as a nickel-titanium alloy or a shape memory polymer.

In any of these embodiments, the intravascular stretching mechanism, or a portion thereof, can include a therapeutic or prophylactic agent, such as a growth-stimulating agent, which can be released in an effective amount to enhance growth of the blood vessel. Another example is an anti-thrombotic agent to minimize the risk of a blood clot during the stretching process. The therapeutic or prophylactic agent can be impregnated in or coated onto the device components, and/or added and released through a lumen in the catheter that delivers the device to its intravascular position.

Methods are provided for distending a blood vessel of a human or animal to induce blood vessel growth. The steps include (i) inserting into an interior lumen portion of a blood vessel the stretching mechanism of the devices described herein; (ii) anchoring the stretching mechanism to the interior lumen portion at at least two positions which are axially remote from one another; and (iii) operating the stretching mechanism to axially stretch the blood vessel between said at least two positions over a period of time effective to induce axial growth of the blood vessel. This operation step could be active (e.g., applying an external force to the mechanism or a component thereof) or passive (e.g., simply releasing an elastic force, such as a spring). The stretching can be performed in vivo or in vitro in a medium for cell growth.

Methods are also provided for forming a vascular graft for a human patient in need thereof. The methods include the steps of distending a donor blood vessel by use of one of the intravascular stretching devices and methods described herein, and then excising a portion of the distended donor vessel, that portion thereby providing a vascular graft. While a variety of blood vessel types could be stretched as described herein, the blood vessel preferably is selected from an internal mammary artery, a femoral artery, a gastroepipolic artery, a gastric artery, a radial artery, and a splenic artery, when stretching the vessel to form a vascular graft.

DETAILED DESCRIPTION OF THE INVENTION

It is known that smooth muscle cells, which dominate the media, the major load bearing layer of the arterial wall, proliferate and increase their production of extracellular matrix in response to mechanical stimulation. It was discovered that this knowledge could be advantageously applied to create an autologous graft of appropriate diameter for coronary bypass or other vascular graft application using an intravascular distension device to stimulate angiogenesis.

The distension device secures the donor blood vessel at different points within the vessel and then distends or stretches the vessel between those points to form an elongated portion. The elongated portion can then be excised for use as a vascular graft. The devices and methods described herein can used to make allogeneic and xenogeneic vascular grafts, as well as the more preferred autogeneic vascular grafts.

The Devices and Methods of Operation

The device includes a stretching mechanism that can be attached to and within a donor blood vessel, and a means for operating the stretching mechanism to cause the vessel to distend (i.e., extend), and an optional controller for controlling the operating means. At least two anchoring points are needed to stretch the blood vessel. In preferred embodiments of the intravascular distension device and method, the axial forces for stretching the blood vessel are applied to at least one element of two or more elements, or portions thereof, that are secured (i.e., anchored) to the interior surface of the blood vessel to be stretched. These elements constitute the intravascular stretching mechanism, and preferably can be delivered into the blood vessel by a catheter for installation and use.

The securing preferably is by frictional engagement, rather than with the use of other possible securing means such as adhesives or sutures. This engagement can be implemented with shape-changing materials, as detailed below, or with non-shape changing materials, which for example, may require balloon dilation to cause at least a portion of the stretching mechanism to expand and engage the interior lumen portion of the blood vessel. As the secured elements are displaced from one another, the blood vessel segment therebetween experiences axial stretching forces.

In a first preferred embodiment, the intravascular stretching mechanism includes a pair of wires, the end portions of which can be anchored within the blood vessel, and a means to displace the wires away from each other and stretch the vessel. The blood vessel can be displaced (i.e., stretched) in rectilinearly, curvilinearly, or in a combination thereof. This displacement can be accomplished by any of a variety of techniques, for example, by mechanical, electromechanical, or hydraulic means.

In a second preferred embodiment, the intravascular stretching mechanism comprises a pair of stents connected by a compression spring, which operates as a means to displace the stents away from each other and stretch the vessel. As used herein, the term "stent" refers to an elastic, expandable, generally cylindrical anchor capable of engaging a blood vessel wall and resisting axial forces; it may or may not be structurally like a conventional stent, which primarily serves to resist radial forces.

It is possible that components of these two different designs can be combined, for example, using a combination of stents and wires to perform the stretching process. It is also envisioned that these anchoring elements can take the form of other suitable structures now known or later developed, as the choice of anchoring elements generally can be considered a matter of design choice.

A. Design Utilizing Anchored Wires

In some embodiments, the device employs two wires anchored within the blood vessel to be stretched. Examples of these are shown in FIGS. 1-5 and described below.

The Device and Components Thereof

Figure 1:
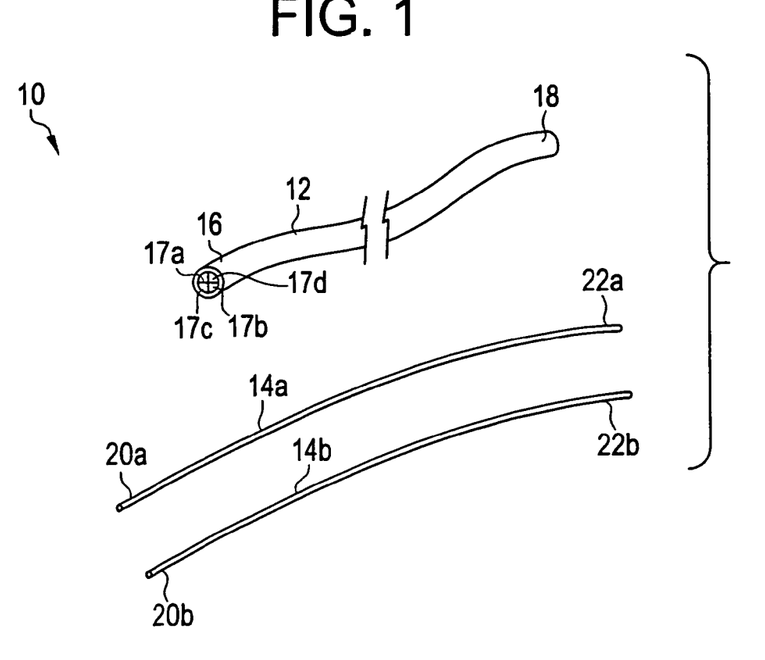
FIG. 1 is a perspective view of the parts of one embodiment of the intravascular device, which includes a multi-lumen catheter, an anchor wire, and stretching wire.

As shown in FIG. 1, a kit 10 includes a multi-lumen catheter 12 and at least two wires: a stretching wire 14a and an anchor wire 14b. The catheter 12 has proximal end 16 and opposed distal end 18, and has four lumens, 17a, 17b, 17c, and 17d.

The catheter and wires can be provided as a kit or an assembled device. The catheter can be a standard, commercially available catheter. The catheter preferably has at least two lumens, one for each of the two wires. Additional lumens can be included for cold saline or other purposes. Selection of the appropriate diameter and length for the catheter will of course depend on the particular blood vessel selected for stretching, as well as on the diameter and number of the anchor wires and stretching wires to be used.

Figure 2A:
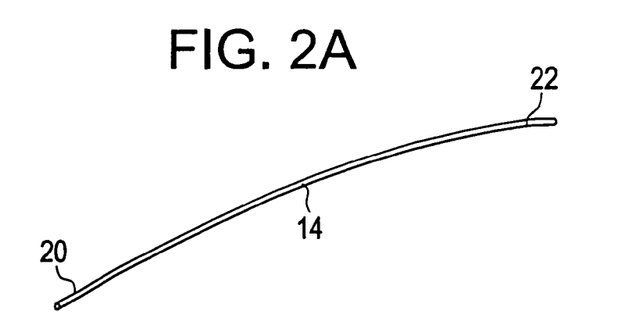
FIG. 2 is a perspective view of a wire having a distal end portion comprising a shape memory material in a straight configuration (FIG. 2A) and in a spiral configuration (FIG. 2B).
Figure 2B:
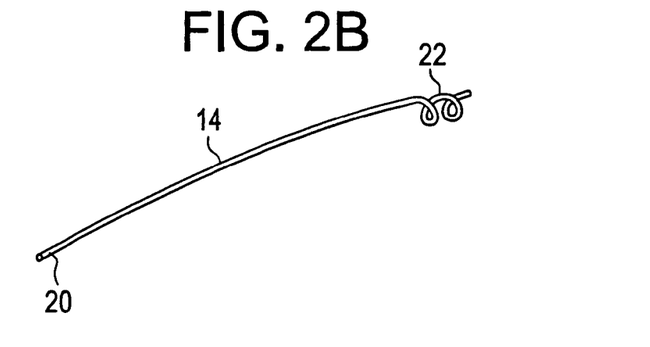

The stretching wire 14a has proximal end portion 20a and distal end portion 22a, and the anchor wire 14b has proximal end portion 20b and distal end portion 22b. Both the stretching wire and the anchor wire must be able to be secured to the interior surface of the blood vessel to be stretched. FIGS. 2A and 2B illustrate a wire 14 that can serve as the anchor wire, the stretching wire, or both. Wire 14 has a proximal end portion 20 and a distal end portion 22. Distal end portion 22 must be changeable from a straight configuration (FIG. 2A) into a second configuration that will frictionally engage the interior surface of the blood vessel. In a preferred embodiment, the second configuration is a spiral, as shown in FIG. 2B. As used herein, the term "spiral" includes any helical, spiral, coiled, cylindrical, or curled shape.

The stretching wire 14a should be of a suitable gauge and material of construction so that it is resistant to buckling when subjected to the pushing (stretching) forces. This gauge and construction can be different from that of the anchor wire 14b, which undergoes a pulling, rather than pushing, force during vessel stretching.

Figure 4A:
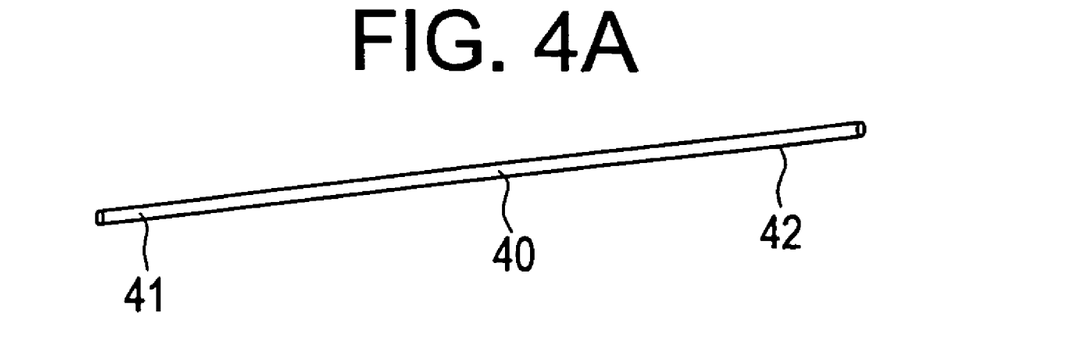
FIG. 4 is a perspective view of a wire having a distal end portion comprising a shape memory material in a straight configuration (FIG. 4A) and in a complex configuration having a spiral end and a compression spring (FIG. 4B).
Figure 4B:
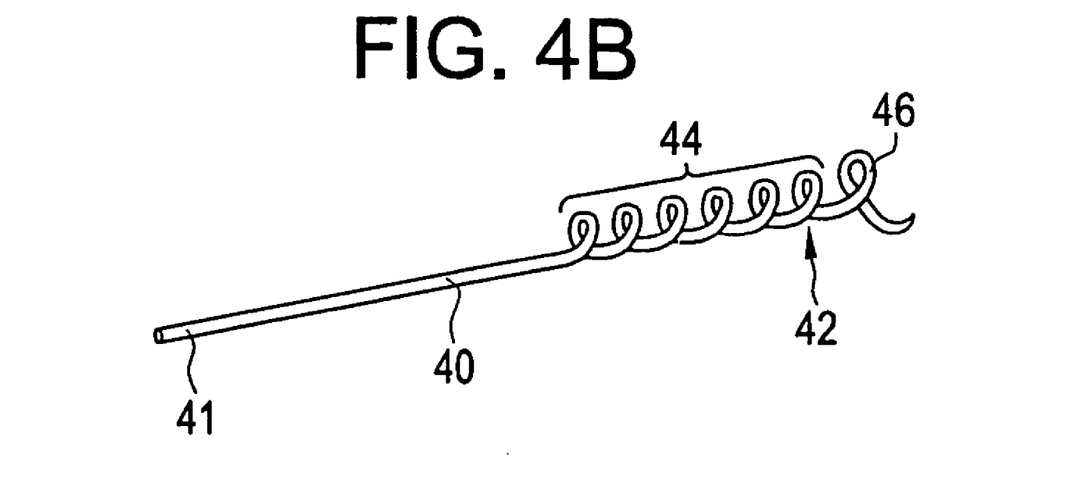

In other embodiments, the stretching wire and/or anchor wire deploy into other, more complex configurations. For example, the stretching wire can deploy (e.g., upon warming to body temperature) into an anchoring spiral with a compression spring, as showing in FIGS. 4A-B. FIG. 4A shows a stretching wire 40, having proximal end 41 and distal end 42, in its straight configuration, for example, at a temperature less than body temperature. FIG. 4B shows the stretching wire 40 with the distal end portion 42 transformed into a compression spring 44 portion and spiral anchor portion 46.

The wires can be fabricated using suitable materials and methods to accomplish the transformation of shape shown. For example, the wires can be maintained in a straight profile with a removable sleeve that snugly fits around the wire. Such a sleeve could simply be slid off the wire following insertion. The sleeve could be a separate component that fits within the catheter lumen or the catheter itself could serve the sleeve function. The shape change of the wire could be due to a spring action inherent in the material of construction of the wire, such that, upon sleeve removal the wire changes into the curled configuration. Such a transformation can occur because of the elastic restorative forces normally exhibited in most metals and polymeric materials, forces that could be made, by one skilled in the art, to straighten a curved wire formed from these materials.

In a preferred embodiment, this configuration-changing function is accomplished by having the wire, or at least the distal end portion thereof, include a suitable shape memory material. Shape memory materials typically have two distinct shapes, and the transition between these shapes can occur in response to various stimuli. A preferred transition stimulus is a change in temperature. For example, distal end 22 of wire 14 can designed to be straight at room temperature, e.g., about 20° C., (FIG. 2A) and to form a spiral shape when warmed to human body temperature, e.g., about 37° C., or above (FIG. 2B). Other transition temperatures can be utilized.

Nickel-titanium alloys (e.g., Ninitol) that exhibit superelastic and shape-memory effects are particularly suitable. Other shape memory alloys and shape memory polymeric materials also can be used. For example, such shape memory materials can be fabricated to change shape from straight to spiral as the wires warm to body temperature following in vivo insertion. Examples of shape memory polymers and other shape memory materials are described, for example, in PCT WO 99/42528 to MIT; U.S. Pat. No. 6,160,084 to Langer et al.; and *Shape Memory Materials*, (Otsuka & Wayman, eds.), Cambridge University Press (October 1999), which are hereby incorporated by reference. Methods for forming or coating wires with such materials are known to those skilled in the art.

In a preferred embodiment, the device is formed of a biodegradable shape memory polymer, such as described in U.S. Pat. No. 6,160,084 to Langer et al. The specific polymer could be tailored to degrade following completion of the stretching procedure. A device formed of such materials preferably would not need to be removed before vessel excision or grafting.

It is important to note that the "memory" of the shape memory material of the compression spring is not limited to axial recovery. The shape memory material can take the form of complex curves (e.g., S-shaped) during their expansion and recovery, thereby creating tortuous paths for the axial blood vessel growth and reducing axial differentiation between the anchoring elements while increasing the arterial path between them. See, e.g., FIG. 8.

Operating Means and Controller

The linear movement of the wires can be driven by a wide variety of forces and driver means known in the art. The movement also may be conducted using mechanical, electromechanical, hydraulic, or other means known for controllably pushing/pulling one structure relative to a second structure. Some of these are described in, or can be adapted from those describe in, U.S. Pat. No. 6,322,553 to Vito, which is hereby incorporated by reference.

The device includes means to operate the stretching mechanism, preferably including a prime mover and electronic drivers for the prime mover. The prime mover can be an electromechanical (active) device, such as a linear motor that operates the stretching mechanism to push and/or pull the distal end of the stretching wire away from the distal end of the anchor wire. The operating means preferably is operably connected to the proximal end of at least the stretching wire.

A rotary motor could also be used to generate the required linear motion, using techniques known in the art. Alternatively, the prime mover can operate hydraulically. An active device generally requires input over time. The prime mover also can be a passive device such as a spring or a combination of a spring and a damper, where stored mechanical energy is used to push and/or pull the anchored portions of the wires away from each other.

Linear or rotary piezo micro-motor devices (actuators) deliver small step sizes, small forces, have relatively simple control electronics and inherent force overload protection. Suitable devices are available from a number of vendors, including Micro Pulse Systems, Inc. Parameters of the operating means include the force applied by the stretching mechanism, the rate and direction of movement of the stretching mechanism, the length of time that the stretching mechanism is operated, and the type of stretching applied (e.g., continuous, cyclical, or intermittent).

The controller controls the operating means. The controller can include a microprocessor that can be activated and programmed to control the stretching process. It preferably can be reprogrammed as needed to control the stretching process, based, for example, on x-ray data or other indications of how the process is proceeding.

The mechanical or hydraulic stretching mechanism works to move the wires apart slowly over a period of up to several weeks. In one embodiment, the passive driver element may be used to provide a pre-determined stretch over time. In another embodiment, the driver may be programmed to operate autonomously, for example to provide a stretch of several centimeters over about one month. Alternatively, cyclic stretching of increasing peak and mean amplitude may be used. Using piezo actuators, activating the driver can produce incremental movements of the mechanical or hydraulic stretching mechanism as small as a few microns. The prime mover is designed to be force limited to preclude overstretching the vessel. Force limitation is inherent if the piezoelectric actuators are used in either embodiment and, in the case of permanent magnetic motors, can be designed into the electronic driver circuit.

Methods of Use

The catheter can be inserted using well-established techniques for catheter insertion. Briefly, a guide wire is inserted using an insertion catheter and is steered to the target blood vessel, usually by using fluoroscopic techniques. The catheter then slides over the guide wire so that its distal end is located in the lumen of the target blood vessel. Insertion of the catheter is facilitated by its radio-opaque nature.

In the methods employing shape memory materials that can be activated by a temperature change, the anchor wire and stretching wire typically will need to be maintained at a temperature below body temperature until their distal ends are correctly positioned inside the target blood vessel lumen. Techniques for accomplishing this temperature control are well known to those skilled in the art. For example, chilled saline can be flowed through one or more of the catheter lumens to maintain the temperature of the wire that is inside a catheter lumen below the activation temperature.

Figure 3A:
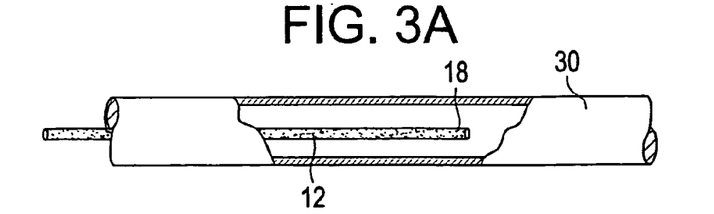
FIGS. 3A-E are partial cross-sectional views of a blood vessel in which one embodiment of the intravascular device is being deployed and operated to stretch the blood vessel, using external force to push an anchored stretching wire away from an anchor wire.
Figure 3B:
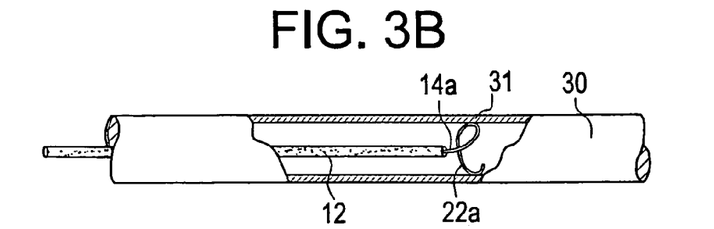

The device described with reference to FIGS. 1 and 2 can be installed and operated as illustrated in FIGS. 3A-E. In these FIGS., blood flow should be from left (proximal) to right (distal). FIG. 3A shows a catheter 12 in an inserted position within target blood vessel 30, such that distal end 18 of catheter 12 is in the desired position for deployment of the stretching wire. As stretching wire 14a is deployed, its distal end portion 22a warms to body temperature and changes to a spiral, expanded configuration and engages circumferentially the interior surface 31 of blood vessel 30, as shown in FIG. 3B. This engagement causes the stretching wire 14a to be secured to the blood vessel 30 and establishes a distal anchoring point therein.

Figure 3C:
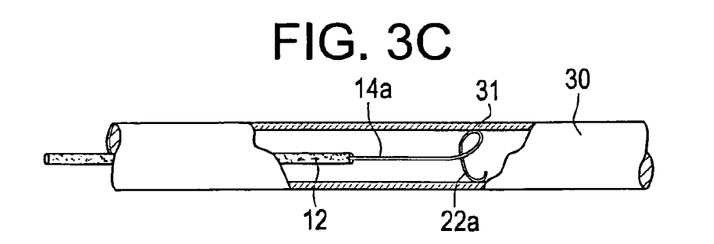
Figure 3D:
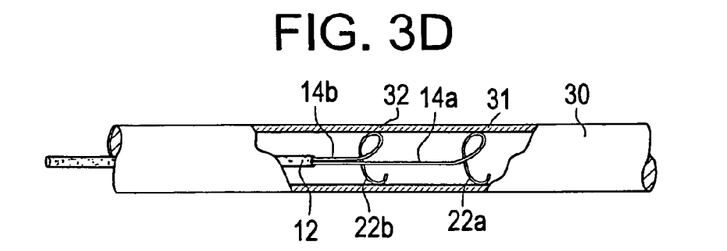

Next, a proximal anchoring point is established. As shown in FIG. 3C, the catheter is first moved proximally (to the left) such that distal end 18 of catheter 12 is in the desired position for deployment of the anchor wire. As anchor wire 14b is deployed, its distal end portion 22b warms to body temperature and changes to a spiral, expanded configuration and engages circumferentially the interior surface 32 of blood vessel 30, as shown in FIG. 3D. This engagement causes the anchor wire 14b to be secured to the blood vessel 30 and establishes a proximal anchoring point therein. These distal and proximal anchoring points, at surfaces 31 and 32, respectively, establish the blood vessel segment to be stretched.

Figure 3E:
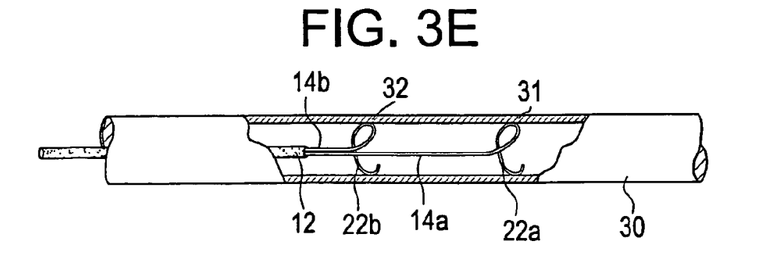

Stretching forces are then applied to one or both of the wires 14a and 14b. Production and control of these stretching forces can be provided as described above. Stretching can be continuous, cyclical, or intermittent, or in a combination thereof. FIG. 3E illustrates that the stretching wire 14a has been pushed and caused the blood vessel 30 to be stretched and grown between points 31 and 32. While the stretching shown in FIG. 3E is linear (or rectilinear), stretching also can occur in curvilinear manner or in a combination of rectilinear and curvilinear stretching.

Figure 5A:
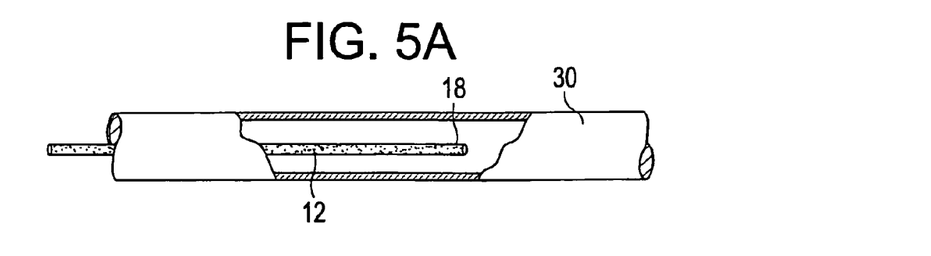
FIGS. 5A-E are partial cross-sectional views of a blood vessel in which a second embodiment of the intravascular device is being deployed and operated to stretch the blood vessel, using an integral compression spring to push an anchored stretching wire away from an anchor wire.
Figure 5B:
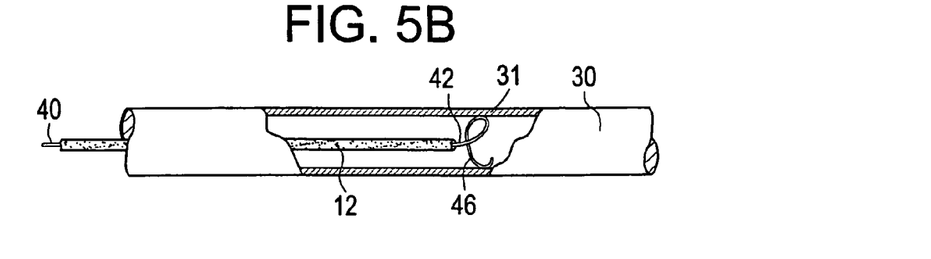

The device described with reference to FIGS. 1 and 3 can be installed and operated as illustrated in FIGS. 5A-E. In these FIGS., blood flow should be from left (proximal) to right (distal). FIG. 5A shows a catheter 12 in an inserted position within target blood vessel 30, such that distal end 18 of catheter 12 is in the desired position for deployment of the stretching wire. As stretching wire 40 is partially deployed, the tip end portion of distal end portion 42 warms to body temperature and changes to a spiral, expanded configuration, forming a spiral 46 which engages circumferentially the interior surface 31 of blood vessel 30, as shown in FIG. 5B. This engagement causes the stretching wire 14a to be secured to the blood vessel 30 and establishes a distal anchoring point therein.

Figure 5C:
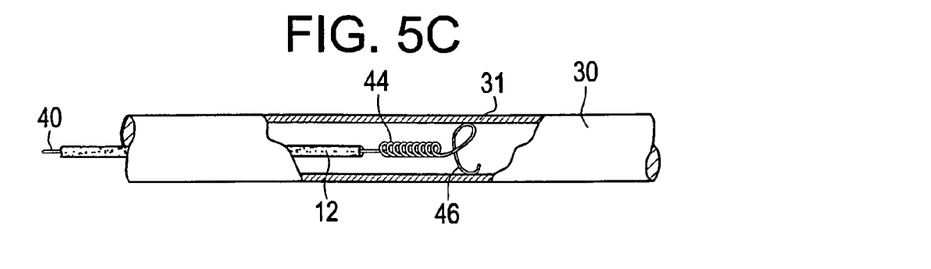

As stretching wire 40 continues to be deployed, an intermediary portion of the distal end portion 42 transforms into a helical configuration operable as a compression spring 44, as shown in FIG. 5C. This compression spring 44 has an outer diameter that is smaller than that of the spiral 46, so that the compression spring 44 does not frictionally engage and become anchored to the blood vessel wall.

Figure 5D:
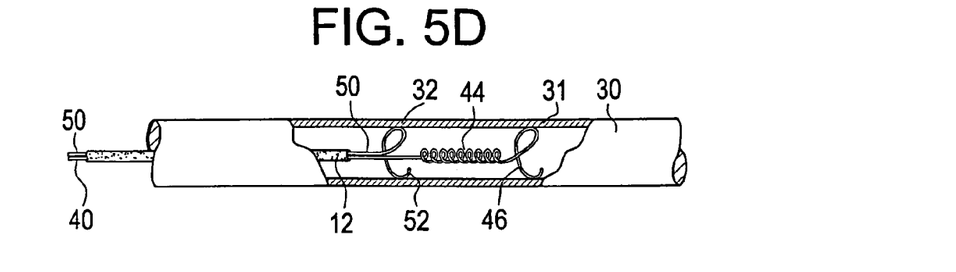

After the compression spring 44 is fully formed, a proximal anchoring point is established. As shown in FIG. 5D, the catheter is first moved proximally (to the left) such that distal end 18 of catheter 12 is in the desired position for deployment of the anchor wire. As anchor wire 50 is deployed, its distal end portion 52 warms to body temperature and changes to a spiral, expanded configuration and engages circumferentially the interior surface 32 of blood vessel 30, as shown in FIG. 3D. This engagement causes the anchor wire 50 to be secured to the blood vessel 30 and establishes a proximal anchoring point therein.

Figure 5E:
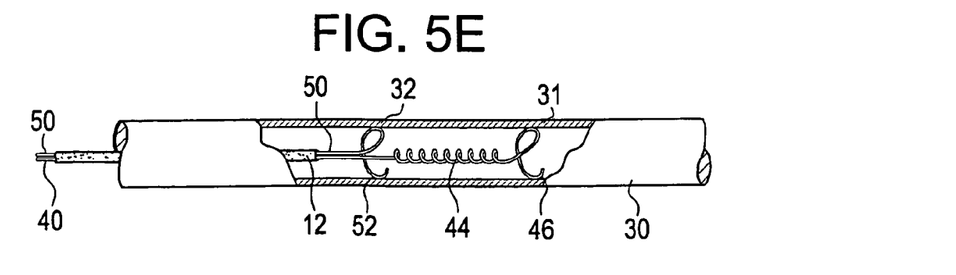

These distal and proximal anchoring points, at surfaces 31 and 32, respectively, establish the blood vessel segment to be stretched. Stretching forces are then applied by the release of compression in spring 44, which stretches the blood vessel 30 as shown in FIG. 5E. It may be convenient in this embodiment to simply leave the catheter in place while stretching occurs.

B. Design Utilizing Combination of Stents and Springs

In another embodiment, the intravascular stretching means comprises a pair of stents, wherein the stents, rather than the wire spirals described above, function as the anchoring elements. While a variety of stent designs are commercially available or otherwise known for use in maintaining blood vessel diameter, the stents of the present methods and devices are designed and used to impart axial forces to increase the length of the vessel.

The Device and Components Thereof

Figure 6A:
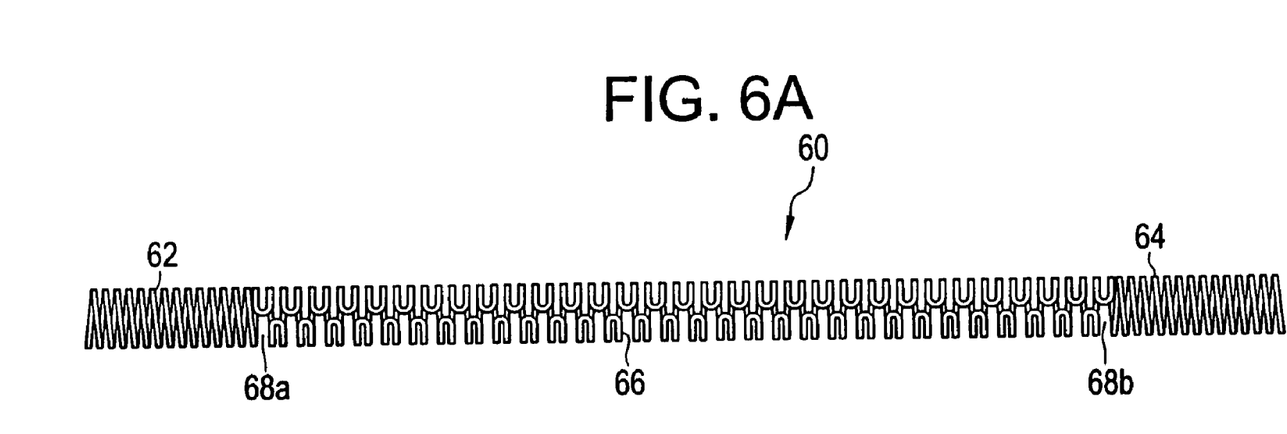
FIG. 6 is a side view of one embodiment of the intravascular stretching device, which includes two stents and an integral compression spring, which comprises a shape memory material, shown in a compressed configuration (FIG. 6A) and in an expanded configuration (FIG. 6B).
Figure 6B:
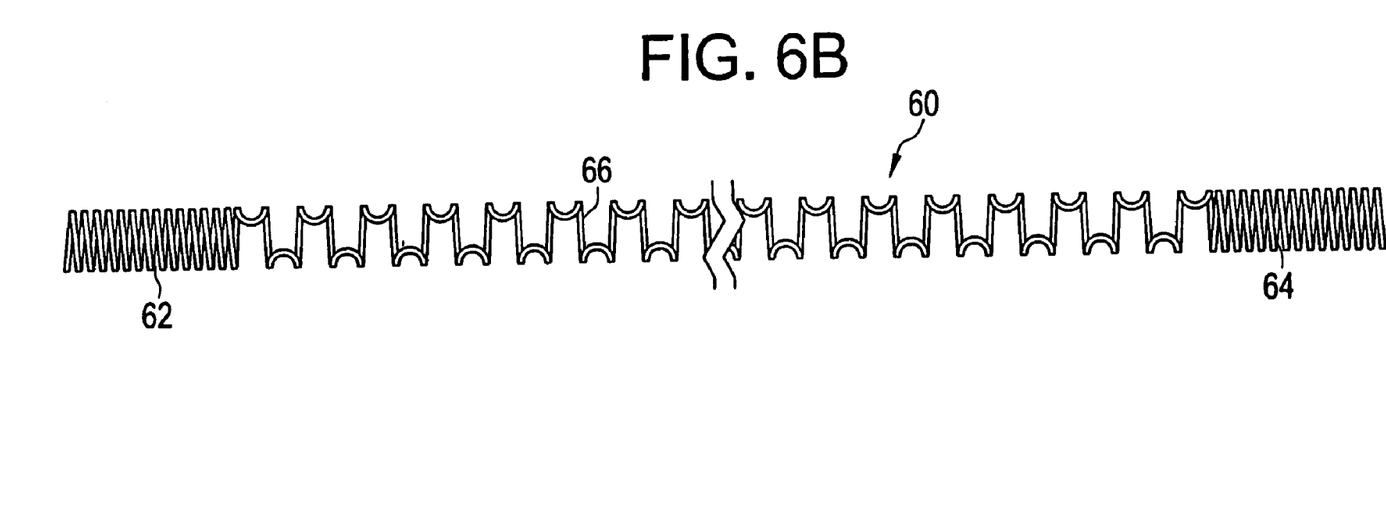

One example of such a design is illustrated in FIGS. 6A-B. FIGS. 6A and 6B show intravascular device 60, which is comprised of a proximal stent 62, a distal stent 64, and a compression spring 66 secured between the distal and proximal stents. One end of the proximal stent 62 is connected to, or integral with, the proximal end 68a of compression spring 66, and one end of the distal stent 64 is connected to, or integral with, the distal end 68b of compression spring 66. FIG. 6A shows device 60 with spring 66 in its compressed configuration, and FIG. 6B shows device 60 with spring 66 in its expanded, or stretched, configuration.

Figure 7:
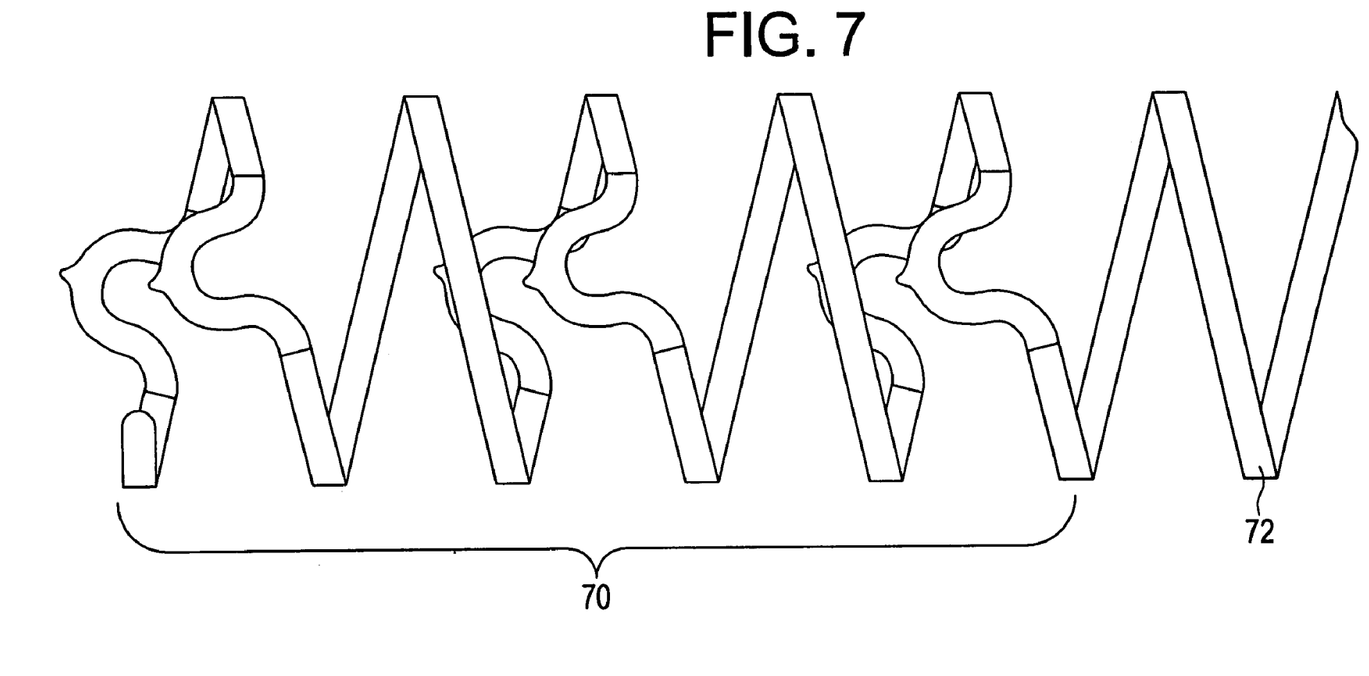
FIG. 7 is a side view of a stent and its integral compression spring, which form part of one embodiment of the intravascular stretching device.

Essentially any stent suitable for vascular implantation can be adapted for use in the present intravascular device. The stent preferably is self-expanding, but also can deployable by other means (e.g., balloon dilation). The stent can be of various types, including but not limited to coil, mesh, and porous structures. One example of an expandable stent is described in U.S. Pat. No. 6,033,436 to Steinke, et al. FIG. 7 shows one embodiment of a proximal or distal stent 70, which is integral with compression spring 72 (only partially shown). This anchoring stent 70 is the structural feature that positively engages the vessel wall (not shown). Numerous other designs are known in the art or can be routinely adapted therefrom. Some configurations are described in U.S. Pat. No. 6,193,744 to Ehr et al. These patents are hereby incorporated by reference.

Preferably, each stent is between about 5 and 20 mm, more preferably about 10 mm, in length. The diameter of the stent desirably is selected for the particular donor vessel, the size of which can vary.

The compression spring can be integrally formed with the stents, or the compression spring can be welded or otherwise attached to the stents following fabrication of each component. Preferably, the entire device is fabricated in one piece, i.e., as a single, contiguous assembly.

The device should be formed of and/or coated with a biocompatible material, as known in the art. Preferably, the compression spring is made of or includes a shape memory material, as describe herein (e.g., nickel-titanium alloys and shape memory polymers). The compression spring can alternatively be made from non-shape memory materials (e.g., titanium, stainless steel, or a biocompatible polymer). The stents preferably are also fabricated from a shape memory material, but may be made from a non-shape memory material, as describe herein.

Methods of Use

The intravascular device is inserted into the target (i.e., donor) blood vessel. Then, the stents are self-expanded (e.g., if they comprise a shape memory material) or are expanded with the use of an installation device, such as a balloon, using or adapting techniques known in the art. The expansion process causes each stent to become frictionally engaged, and thus anchored, to a circumferential portion of the interior surface of the blood vessel. The stents are anchored in positions such that the spring therebetween is in compression. The spring thus exerts an axial, expansion force causing the section of blood vessel between the anchor points to be stretched. The expansion of the compression spring thus causes the length of that blood vessel section to lengthen.

Figure 8A:
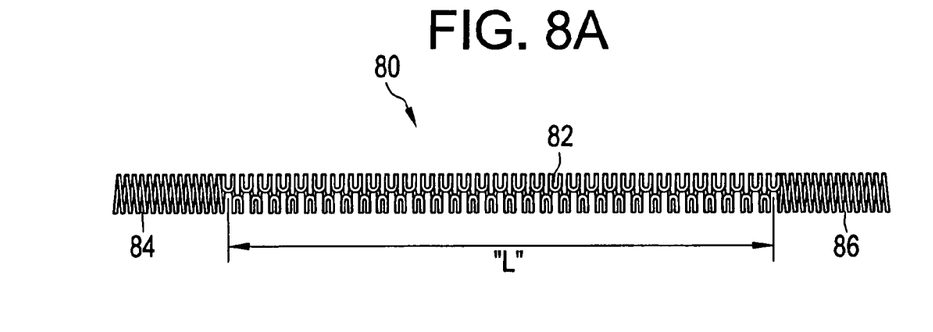
FIG. 8 is a side or plan view of a one embodiment of the intravascular stretching device, which includes two stents and an integral compression spring shown in a compressed configuration (FIG. 8A) and in a curvilinear expanded configuration (FIG. 8B).
Figure 8B:
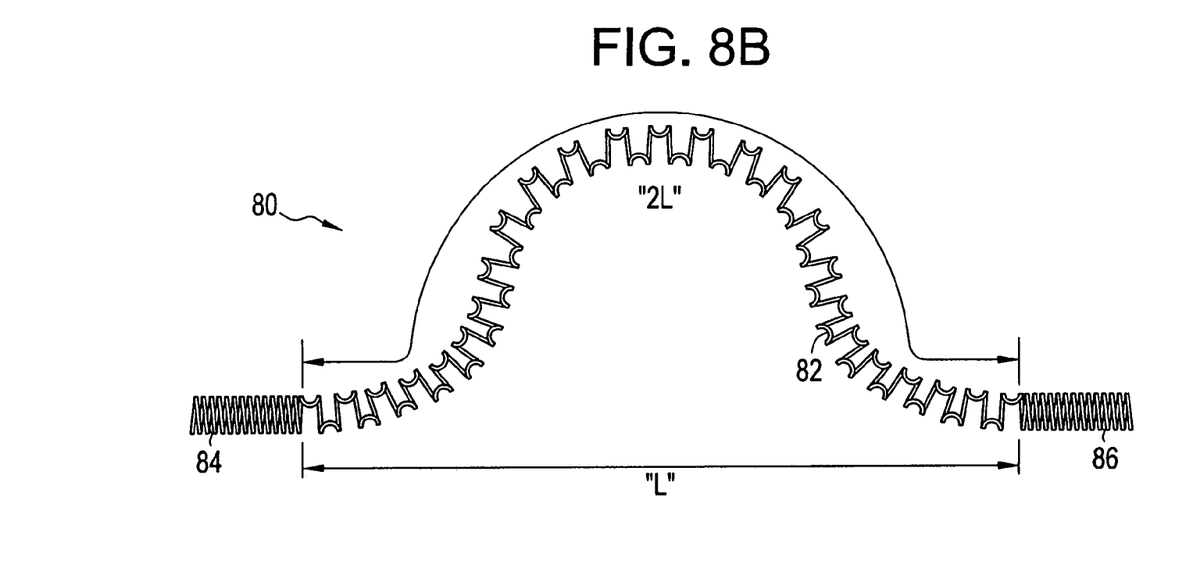

FIGS. 8A-B illustrate one embodiment of a stent-type stretching device 80 comprising stents 84 and 86 with compression spring 82 in a compressed configuration (FIG. 8A) and with the compression spring 82 in an expanded or stretched configuration (FIG. 8B). FIG. 8B illustrates how a blood vessel could be stretched in a curvilinear manner to twice the original length, L. A stent-type device also could expand to stretch in a linear (or rectilinear) manner or in combination of curvilinear and rectilinear motion.

C. Other Design Features

The methods and devices described herein optionally can include growth factors or other growth stimulating agents (e.g., hormones) to further enhance blood vessel growth. For example, such growth stimulating agents can be delivered to the blood vessel by impregnating the materials forming the wires, stents or other device components. Alternatively or additionally, the device components can be provided with a suitable coating or reservoirs that can contain and controllably release such agents during the extension process. Examples of growth factors include vascular endothelial growth factor (VEGF), endothelial cell growth factor (ECGF), basic fibroblast growth factor (bFGF), and platelet derived growth factor (PDGF). Biocompatible polymeric materials for controlled release that are known in the art for drug delivery (see e.g., U.S. Pat. No. 5,879,713 to Roth et al.) can be adapted for use with the devices described herein. The devices and methods also can be used in combination with external electric, magnetic, or electromagnetic fields applied as a growth stimulus. See e.g., U.S. Pat. No. 4,846,181 to Miller.

The devices also can optionally include appropriate drugs (e.g., therapeutic or prophylactic agents) impregnated into or coated to structural components, for example to minimize infections, thrombosis, inflammatory reactions, scar tissue formation, adhesion formation, and/or other adverse tissue reactions. For example, where tissue growth is to be avoided, certain antifibrotic agents may be present, such as 5-fluourouracil or mitomycin. The device may be more generally provided with coatings that are antibiotic or anti-inflammatory.

The intravascular stretching device also can be designed to limit adhesion formation while installed in the blood vessel. For example, the wires, stents, compression springs, or other components can be impregnated or coated with materials selected to reduce adhesion formation as known in the art. Examples of such coating materials include, but are not limited to, parylene, polytetrafluoroethylene (e.g., TEFLON™) and chromium (e.g., ME-92™, Armoloy Corp.), which can be used to coat a variety of other metal and polymer substrates.

Application of the Distension Devices and Methods

The present devices and methods are useful for forming a vascular graft by axially stretching (i.e., distending or extending) a donor blood vessel to stimulate growth. This stretching can performed in vivo or in vitro.

While an autologous graft is preferred, the devices and methods described herein also can be applied to an artery from another human or other animal, including transgenic animals genetically engineered to have tissues that will not be rejected by humans. For example, a distended artery from a transgenic pig might be used to provide a xenogeneic arterial graft in a human.

The devices and methods can be sized to stretch blood vessels (e.g., veins, arteries) of essentially any size and located in or excised from a variety of sites in the body of the patient or donor or animal. Preferred blood vessels include, but are not limited to, the internal mammary arteries, the gastroepipolic artery, the gastric artery, the radial artery, the femoral artery, and the splenic artery. Other arteries and veins may also be suitable blood vessels for use with the methods and devices.

In a preferred embodiment of the in vivo distension method, the stretching mechanism is inserted into a donor blood vessel, for example using a catheter, and vessel distension effected over a period of time. Then the stretching mechanism is withdrawn, and a portion of the donor blood vessel section is surgically removed. The ends of the donor vessel can then be sutured end to end to repair the donor vessel, as is commonly done in vascular repair without complication. Some blood vessels used for coronary bypass surgery, such as the gastroepipolic and radial arteries, can be removed with minimal morbidity such that repair is unnecessary. The removed blood vessel section is then ready for use as a graft in a patient in need thereof, who preferably is the same patient supplying the donor vessel.

Grafts for coronary by-pass surgery are typically between about 10 cm and 15 cm in length, whereas grafts for by-pass in the peripheral circulation are typically about 25 cm or more in length. Those of skill in the art can readily optimize the rate of vessel distension. Distension rates can be linear or nonlinear, and may average, for example, between about 5 and 10 mm/day.

The device can also be used for in vitro distension. Currently, a short segment of blood vessel can be salvaged during conventional bypass surgery and an in vitro organ culture or bioreactor system can be used to grow sufficient graft tissue for a second surgery. Such surgeries represent about 30% of all bypass operations. The methods and devices described herein can be adapted to work with such surgeries, to increase the length of graft material and/or to reduce the required length of the salvaged segment. Stretched blood vessels can be effectively preserved for bypass surgery, for example, using known cryogenic or freeze-drying techniques.

In this method, a portion of a donor blood vessel (e.g., shorter than that needed for a graft) is surgically excised from the patient in need of the graft, and then the vessel portion is stretched over a period of time in vitro in a medium for cell growth, for example, as in a bioreactor. As used herein, the phrase "medium for cell growth" includes any in vitro system for facilitating cell division, extracellular matrix formation, and growth of vessel tissue. See, for example, U.S. Pat. No. 5,899,936 to Goldstein; U.S. Pat. No. 5,879,875, to Wiggins, et al.; and U.S. Pat. No. 5,888,720 to Mitrani, which describe techniques for organ and tissue culture which can be adapted to the methods described herein. All or a portion of the distended vessel is then ready for use as a graft in the patient. Where the donor is the recipient of the graft, the result using either approach advantageously is a totally autologous, living vascular graft.

Modifications and variations of the present invention will be obvious to those of skill in the art from the foregoing detailed description. Such modifications and variations are intended to come within the scope of the following claims.

We claim:

1. An implantable medical device for distending a blood vessel to induce axial growth of the blood vessel comprising:
an intravascular stretching mechanism securable to an interior luminal surface of a blood vessel in vivo; and
a means for operating the intravascular stretching mechanism in vivo to cause the vessel to stretch and grow axially;
wherein the intravascular stretching mechanism comprises:
an anchoring wire having a distal end portion; and
a stretching wire having a distal end portion;
wherein the distal end portions are separately anchorable to the luminal surface at positions axially remote from one another.

2. The implantable medical device of claim 1, wherein the distal end portion of the anchoring wire, the distal end portion of the stretching wire, or both, comprise a shape memory material.

3. The implantable medical device of claim 2, wherein the shape memory material comprises a shape memory alloy or a shape memory polymer.

4. The implantable medical device of claim 2, wherein in response to a change in temperature effective to trigger a change in the shape memory material, the distal end portion of the stretching wire changes, the distal end portion of the anchoring wire, or both distal end portions, change, from a substantially straight form into a spiral configuration for securing engagement with the interior luminal surface of the blood vessel.

5. The implantable medical device of claim 4, wherein in response to a change in temperature effective to trigger a change in the shape memory material, an intermediary portion of the stretching wire changes from a substantially straight form into a helical configuration operable as a compression spring.

6. The implantable medical device of claim 1, further comprising a catheter having at least two lumens extending between a proximal end and a distal end, one of said at least two lumens being suitable for delivering the stretching wire into the blood vessel lumen, and another of said at least two catheter lumens being suitable for delivering the anchor wire into the blood vessel lumen.

7. The implantable medical device of claim 1, wherein the means for operating comprises a prime mover that is mechanically, electromechanically, or hydraulically driven.

8. The implantable medical device of claim 1, wherein the means for operating the stretching mechanism is capable of causing an axial stretching force to be continuously applied to the blood vessel.

9. The implantable medical device of claim 1, wherein the means for operating the stretching mechanism is capable of causing an axial stretching force to be intermittently applied to the blood vessel.

10. The implantable medical device of claim 1, wherein the means for operating the stretching mechanism comprising a controller.

11. An implantable medical device for distending a blood vessel to induce axial growth of the blood vessel comprising:
an intravascular stretching mechanism securable to an interior luminal surface of a blood vessel in vivo; and
a means for operating the intravascular stretching mechanism in vivo to cause the vessel to stretch and grow axially;
wherein the intravascular stretching mechanism comprises a first stent, a second stent, and a compression spring operably connected to the first stent and the second stent, the first and second stents being separately anchorable to the interior luminal surface of the blood vessel at positions axially remote from one another.

12. The implantable medical device of claim 11, wherein the first stent, the second stent, the compression spring, or a combination thereof, comprises a shape memory material.

13. The implantable medical device of claim 12, wherein the shape memory material comprises a shape memory alloy or a shape memory polymer.

14. The implantable medical device of claim 1, further comprising at least one therapeutic or prophylactic agent for release in vivo.

15. The implantable medical device of claim 14, wherein the therapeutic or prophylactic agent comprises a growth stimulating agent.

16. The implantable medical device of claim 1, wherein all or a portion of the intravascular stretching mechanism is radio-opaque.

17. A device for distending a blood vessel in vivo to induce axial growth of the blood vessel comprising:
an intravascular stretching mechanism which comprises
an anchoring wire having a distal end portion, and
a stretching wire having a distal end portion,
wherein the distal end portions are separately anchorable to a luminal surface of a blood vessel in vivo at positions axially remote from one another; and
a prime mover for operating the intravascular stretching mechanism to cause the vessel to stretch in vivo and grow axially.

18. The device of claim 17, wherein the prime mover comprises an electro-mechanical device adapted to push and/or to pull the distal end of the stretching wire away from the distal end of the anchor wire.

19. The device of claim 17, wherein the prime mover comprises at least one spring or a combination of a spring and a damper.

* * * * *